United States Patent

Yabe et al.

(10) Patent No.: US 9,526,144 B2
(45) Date of Patent: Dec. 20, 2016

(54) LIGHT SOURCE APPARATUS AND ENDOSCOPE APPARATUS

(71) Applicant: OLYMPUS CORPORATION, Tokyo (JP)

(72) Inventors: Yusuke Yabe, Chofu (JP); Tomoya Takahashi, Hachioji (JP); Yusuke Yoshida, Fussa (JP); Masato Toda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/040,089

(22) Filed: Feb. 10, 2016

(65) Prior Publication Data

US 2016/0157322 A1 Jun. 2, 2016

Related U.S. Application Data

(63) Continuation of application No. PCT/JP2014/071665, filed on Aug. 19, 2014.

(30) Foreign Application Priority Data

Aug. 23, 2013 (JP) ................................ 2013-173570

(51) Int. Cl.
*H05B 33/08* (2006.01)
*G02B 23/24* (2006.01)
(Continued)

(52) U.S. Cl.
CPC ....... *H05B 33/0884* (2013.01); *A61B 1/00002* (2013.01); *A61B 1/0684* (2013.01);
(Continued)

(58) Field of Classification Search
CPC ..... A61B 1/00002; A61B 1/0684; A61B 1/12; F21V 29/54; G02B 23/2461; H04N 2005/2255; H04N 5/2256; H04N 5/2257; H04N 5/2354; H05B 33/0845; H05B 33/0884
(Continued)

(56) References Cited

U.S. PATENT DOCUMENTS

2012/0123213 A1* 5/2012 Seto ..................... A61B 1/0638
600/178
2013/0070208 A1* 3/2013 Nakanishi .............. G03B 21/16
353/31

FOREIGN PATENT DOCUMENTS

EP 2452611 A1 5/2012
JP 2005-277877 A 10/2005
(Continued)

OTHER PUBLICATIONS

International Search Report dated Nov. 25, 2014 issued in PCT/JP2014/071665.
(Continued)

*Primary Examiner* — Behrooz Senfi
(74) *Attorney, Agent, or Firm* — Scully, Scott, Murphy & Presser, P.C.

(57) ABSTRACT

A light source apparatus includes a cooling device configured to be able to cool a semiconductor light-emitting device, a light-emitting device drive section that supplies a semiconductor light-emitting device drive signal to the semiconductor light-emitting device, a cooling device drive section that supplies a cooling device drive signal to the cooling device, a semiconductor light-emitting device drive control section that sets a duty ratio of the semiconductor light-emitting device drive signal and controls an amount of light emission of the semiconductor light-emitting device, and a cooling device drive control section that generates the cooling device drive signal having a same duty ratio as the duty ratio of the semiconductor light-emitting device drive (Continued)

signal and having timing synchronized with the semiconductor light-emitting device drive signal and adjusts a signal level of the cooling device drive signal based on a measurement result of a temperature of the semiconductor light-emitting device.

6 Claims, 4 Drawing Sheets

(51) Int. Cl.
    *A61B 1/00*     (2006.01)
    *A61B 1/06*     (2006.01)
    *A61B 1/12*     (2006.01)
    *F21V 29/54*     (2015.01)
    *H04N 5/225*     (2006.01)
    *H04N 5/235*     (2006.01)

(52) U.S. Cl.
    CPC ................. *A61B 1/12* (2013.01); *F21V 29/54* (2015.01); *G02B 23/2461* (2013.01); *H04N 5/2256* (2013.01); *H04N 5/2257* (2013.01); *H04N 5/2354* (2013.01); *H05B 33/0845* (2013.01); *H04N 2005/2255* (2013.01)

(58) Field of Classification Search
    USPC .............................................. 315/117; 348/69
    See application file for complete search history.

(56) References Cited

FOREIGN PATENT DOCUMENTS

| | | |
|---|---|---|
| JP | 2007-149469 A | 6/2007 |
| JP | 2010-258432 A | 11/2010 |
| JP | 2012-105784 A | 6/2012 |
| JP | 2012-253175 A | 12/2012 |

OTHER PUBLICATIONS

Japanese Office Action dated Jun. 3, 2015 issued in JP 2015-506034.

\* cited by examiner

LIGHT SOURCE APPARATUS AND ENDOSCOPE APPARATUS

CROSS REFERENCE TO RELATED APPLICATION

This application is a continuation application of PCT/JP2014/071665 filed on Aug. 19, 2014 and claims benefit of Japanese Application No. 2013-173570 filed in Japan on Aug. 23, 2013, the entire contents of which are incorporated herein by this reference.

BACKGROUND OF THE INVENTION

1. Field of the Invention

The present invention relates to a light source apparatus suitable for an endoscope and an endoscope apparatus.

2. Description of the Related Art

Conventionally, endoscopes are widely used which are designed to observe a region to be examined and conduct various treatments by inserting an elongated endoscope into a body cavity or the like. For such endoscopes, light source apparatuses are used to perform intracavitary photographing. In recent years, light source apparatuses may also have been used which adopt a semiconductor light source such as an LED as a light emitting section. Such light source apparatuses can perform light adjustment control of an LED through PWM control that changes a duty ratio of drive pulses or current control that changes an LED current.

The light source apparatuses using such LED light sources generate heat according to the amount of light emission and the light quantity fluctuates due to a temperature variation during heat generation. Thus, Japanese Patent Application Laid-Open Publication No. 2007-149469 (hereinafter referred to as "Document 1") discloses an apparatus that cools an LED using a Peltier element. The apparatus according to Document 1 drives a Peltier element using a periodic pulse current that rises earlier than the rise of a pulse current of a drive current of the LED and thereby enables cooling to be performed following heat generation of the pulsating LED.

SUMMARY OF THE INVENTION

A light source apparatus according to the present invention includes a semiconductor light-emitting device, a cooling device configured to be able to cool the semiconductor light-emitting device, a semiconductor light-emitting device drive section that supplies, to the semiconductor light-emitting device, a semiconductor light-emitting device drive signal for causing the semiconductor light-emitting device to emit light, a cooling device drive section that supplies, to the cooling device, a cooling device drive signal for causing the cooling device to cool the semiconductor light-emitting device, a semiconductor light-emitting device drive control section that sets a duty ratio of the semiconductor light-emitting device drive signal and controls an amount of light emission of the semiconductor light-emitting device, a temperature sensor that measures a temperature of the semiconductor light-emitting device, and a cooling device drive control section that controls the cooling device drive section so as to generate the cooling device drive signal having a same duty ratio as the duty ratio of the semiconductor light-emitting device drive signal set by the semiconductor light-emitting device drive control section and having timing synchronized with the semiconductor light-emitting device drive signal and controls the cooling device drive section so as to adjust a signal level of the cooling device drive signal based on a measurement result of the temperature sensor.

An endoscope apparatus according to the present invention includes an endoscope, a semiconductor light-emitting device that generates illuminating light to be supplied to the endoscope, a cooling device configured to be able to cool the semiconductor light-emitting device, a semiconductor light-emitting device drive section that supplies, to the semiconductor light-emitting device, a semiconductor light-emitting device drive signal for causing the semiconductor light-emitting device to emit light, a cooling device drive section that supplies, to the cooling device, a cooling device drive signal for causing the cooling device to cool the semiconductor light-emitting device, a semiconductor light-emitting device drive control section that sets a duty ratio of the semiconductor light-emitting device drive signal and controls an amount of light emission of the semiconductor light-emitting device, a temperature sensor that measures a temperature of the semiconductor light-emitting device, and a cooling device drive control section that controls the cooling device drive section so as to generate the cooling device drive signal having a same duty ratio as the duty ratio of the semiconductor light-emitting device drive signal set by the semiconductor light-emitting device drive control section and having timing synchronized with the semiconductor light-emitting device drive signal and controls the cooling device drive section so as to adjust a signal level of the cooling device drive signal based on a measurement result of the temperature sensor.

DETAILED DESCRIPTION OF THE PREFERRED EMBODIMENTS

Hereinafter, an embodiment of the present invention will be described in detail with reference to the accompanying drawings.

Figure 1:
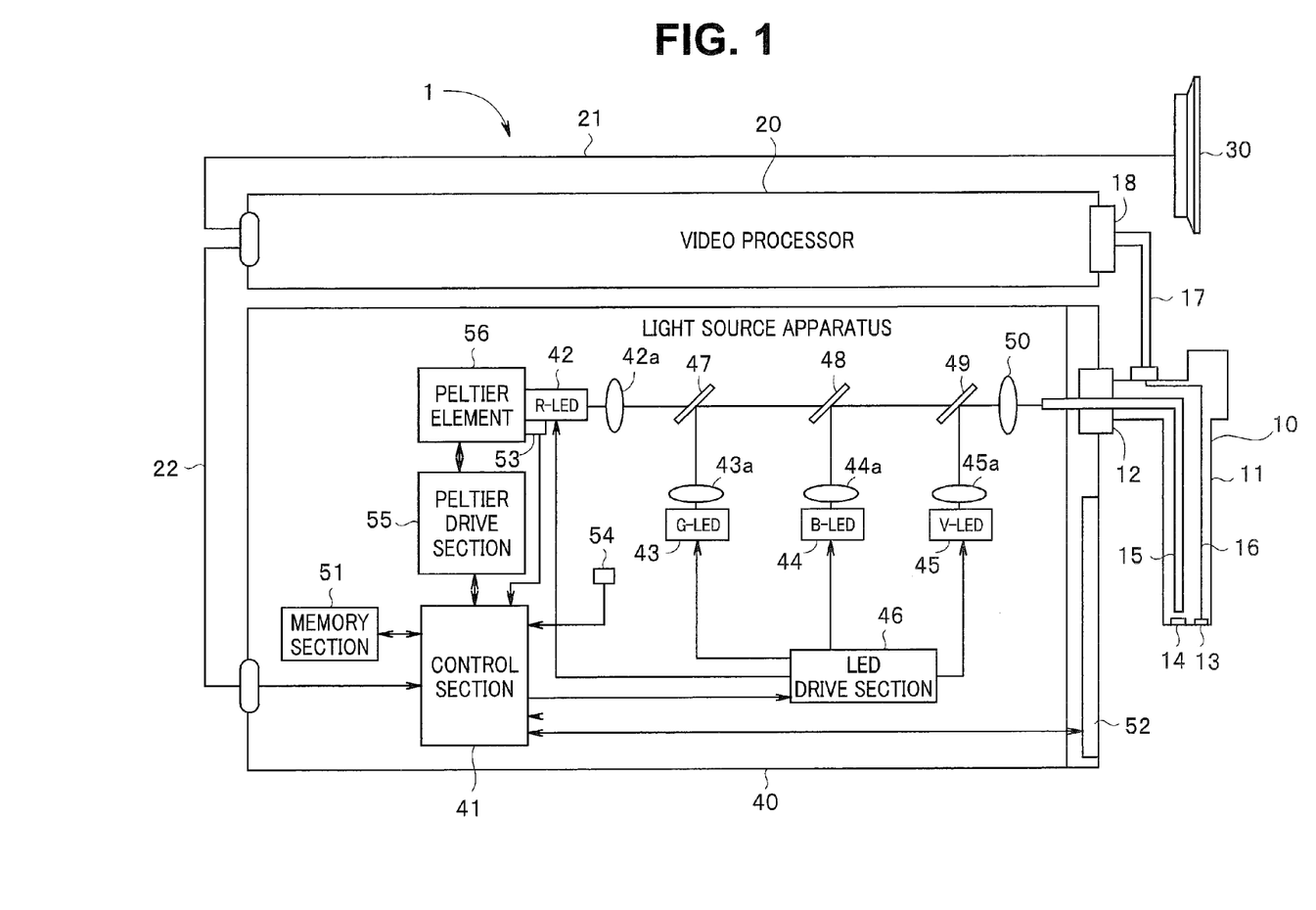
FIG. 1 is a block diagram illustrating a light source apparatus according to an embodiment of the present invention.

FIG. 1 is a block diagram illustrating a light source apparatus according to an embodiment of the present invention. The present embodiment is a light source apparatus applied to an endoscope system including an endoscope, a video processor and a monitor.

An endoscope system 1 is constructed of an endoscope 10, a video processor 20, a monitor 30 and a light source apparatus 40. The endoscope 10 includes an elongated insertion portion 11 that can be inserted into a luminal interior on a distal end side and a proximal end side thereof is detachably connected to the light source apparatus 40 via a connector 12.

The endoscope 10 is detachably connected to the video processor 20 via a cable 17 and a connector 18. Thus, different types of endoscopes can be attached to the light source apparatus 40 and the video processor 20.

An image pickup device 13 for picking up video images of an object such as a luminal interior and a lens 14 for irradiating the object with light from the light source apparatus 40 are disposed at a distal end of the insertion portion 11. Illuminating light transmitted via the light guide 15 from the light source apparatus 40 is radiated onto the object through the lens 14. The image pickup device 13 is constructed of a CCD, a CMOS sensor or the like, causes return light from the object to enter an image pickup surface thereof, photoelectrically converts the incident optical image of the object and sequentially outputs image pickup outputs based on stored charge.

The image pickup device 13 operates by being supplied with a drive signal including a synchronization signal supplied from the video processor 20 and supplies image pickup outputs to the video processor 20 via a signal line 16.

The video processor 20 applies predetermined signal processing to the image pickup outputs and generates a video signal that can be displayed on the monitor 30. A video signal from the video processor 20 is supplied to the monitor 30 via a cable 21. Thus, an endoscope image based on the image pickup outputs can be displayed on a display screen of the monitor 30.

Furthermore, the video processor 20 can control the light source apparatus 40 so that brightness of a picked-up image becomes target brightness. The video processor 20 is designed to output information on a ratio of the brightness obtained from the picked-up image and the target brightness to the light source apparatus 40 as brightness control information. The brightness control information is supplied to a control section 41 of the light source apparatus 40 via a cable 22.

The light source apparatus 40 has an LED (R-LED) 42 that generates red light, an LED (G-LED) 43 that generates green light, an LED (B-LED) 44 that generates blue light and an LED (V-LED) 45 that generates violet light. Note that although the present embodiment describes an example adopting LEDs that generate light of four colors, the types of colors and the number of colors are not limited to those of the present embodiment, but, for example, an LED that generates amber light may also be added to FIG. 1.

Lenses 42a to 45a are arranged on optical axes of emitted light beams of each of LEDs 42 to 45 respectively. The respective lenses 42a to 45a transform the emitted light beams of the LEDs 42 to 45 into substantially parallel light beams respectively and output the parallel light beams. Dichroic filters 47 to 49 that constitute an optical path section are arranged on the optical axis of the lens 42a that causes the light to be emitted from the R-LED 42. The light from the G-LED 43 is also made incident on the dichroic filter 47 via the lens 43a. The light from the B-LED 44 is also made incident on the dichroic filter 48 via the lens 44a and the light from the V-LED 45 is also made incident on the dichroic filter 49 via the lens 45a.

The dichroic filter 47 reflects the light from the G-LED 43 and passes the light from the R-LED 42. The dichroic filter 48 reflects the light from the B-LED 44 and passes the transmitted light from the dichroic filter 47. The dichroic filter 49 reflects the light from the V-LED 45 and passes the transmitted light from the dichroic filter 48.

Thus, the light beams from the LEDs 42 to 45 are synthesized by the dichroic filters 47 to 49. The synthesized light from the dichroic filter 49 is made incident on the light guide 15 via a lens 50. Note that although the arrangement order of the LEDs 42 to 45 can be changed by appropriately setting characteristics of the dichroic filters 47 to 49, the setting of characteristics of the dichroic filters is easier if the LEDs 42 to 45 are arranged in order of wavelength bands of the emitted light beams.

The respective LEDs 42 to 45 are driven to turn on by an LED drive section 46. The LED drive section 46 generates a PWM pulse which is a drive signal to drive each LED under the control of the control section 41. Note that each LED 42 to 45 is designed to emit light at an amount of light emission corresponding to a duty ratio and amperage of PWM pulses from the LED drive section 46. The control section 41 outputs light adjustment information for controlling the respective LEDs 42 to 45 to the LED drive section 46, and thereby controls the duty ratios of PWM pulses and performs light adjustment control over the respective LEDs 42 to 45.

The control section 41 generates light adjustment information so as to allow the amounts of light emission of the respective LEDs 42 to 45 to maintain a predetermined color balance. The color balance among the respective LEDs 42 to 45 needs to be determined according to spectral sensitivity characteristics of the endoscope 10. A memory section 51 of the light source apparatus 40 stores information on light quantity ratios to be generated in the respective LEDs 42 to 45 according to spectral sensitivity characteristics of the endoscope 10 to achieve an optimum color balance. The control section 41 outputs control information for controlling the respective LEDs 42 to 45 to the LED drive section 46 based on the information on the light quantity ratios stored in the memory section 51.

Note that the memory section 51 has been described as storing information on light quantity ratios of the respective LEDs to obtain an optimum color balance, but the endoscope 10 may also be attached to the video processor 20 and the light source apparatus 40 so that information on the light quantity ratio is read from the endoscope 10 and set in the control section 41.

In order to obtain an optimum color balance, information on light quantity ratios of the respective LEDs needs only to be inputted to the control section 41 and the memory section 51 need not always be provided. The light source apparatus 40 is provided with an operation panel 52, and the operation panel 52 can output signals based on the user operation to the control section 41. Using the operation panel 52 allows information on the light quantity ratios to be inputted. Moreover, the operation panel 52 is provided with a display section, which is not shown, and can display current set values or the like.

The control section 41 controls light quantities of the respective LEDs 42 to 45 while maintaining the light quantity ratio at which the optimum color balance is obtained based on brightness control information from the video processor 20. For example, the control section 41 can acquire light adjustment information for controlling the G-LED 43 by causing the memory section 51 to store light adjustment information corresponding to a light quantity value of the G-LED 43 to be set according to the brightness control information and reading the light adjustment information stored in the memory section 51 based on the brightness control information. Furthermore, the control section 41 can obtain light adjustment information of the other LEDs 42, 44 and 45 based on the information on the light quantity ratios stored in the memory section 51.

The light adjustment information obtained by the control section 41 is to control duty ratios of PWM pulses to be supplied to the respective LEDs 42 to 45. The LED drive section 46 generates PWM pulses at duty ratios specified in the light adjustment information and supplies the PWM pulses to the respective LEDs 42 to 45. This causes the respective LEDs 42 to 45 to be pulse-driven at duty ratios based on the brightness control information and light quantity ratios, and emit light with desired brightness.

In the present embodiment, the R-LED 42 is provided with a Peltier element 56, which is a thermoelectric conversion element for cooling. The R-LED 42 includes a substrate, which is not shown, and a light emitting section disposed on the substrate, and the Peltier element 56 is disposed, for example, on the back side of the substrate. The Peltier element 56 is a cooling member using a heat absorption/heat dissipation phenomenon produced by a current flowing through a pn junction and the R-LED 42 is cooled by causing the cooling surface of the Peltier element 56 to contact the back side of the substrate of the R-LED 42.

Cooling effects of the Peltier element 56 are controlled by the current value of a drive current flowing through the Peltier element 56. Under the control of the control section 41, a Peltier drive section 55 controls the current value of the drive current flowing through the Peltier element 56 and thereby controls the cooling of the R-LED 42.

In the present embodiment, the control section 41 outputs a control signal to the Peltier drive section 55 so as to cause a current to flow through the Peltier element 56 at a duty ratio that matches the duty ratio of the PWM pulse for driving the R-LED 42 and in synchronization with the PWM pulse. That is, the Peltier element 56 causes a drive current to flow and delivers cooling effects for a period during which a pulsed LED current flows through the R-LED 42. Thus, according to the present embodiment, since driving of the R-LED 42 is in full synchronization with driving of the Peltier element, cooling by the Peltier element 56 is performed for a period during which the R-LED 42 is on and generating heat, thus making it possible to suppress a temperature rise due to light emission of the R-LED 42.

However, the amount of light emission of the R-LED 42 significantly varies depending on an observation mode or the like in endoscope illumination applications. For this reason, there may be cases where cooling effects of the Peltier element 56 are not sufficient or cooling becomes excessive.

Therefore, the present embodiment measures an actual temperature and controls the current value of a drive current of the Peltier element 56 based on the measurement result. The light source apparatus 40 is provided with thermistors 53 and 54. The thermistor 53 is disposed in the vicinity of the R-LED 42, measures a temperature in the vicinity of the R-LED 42 and outputs the measurement result to the control section 41. The thermistor 54 is disposed at an appropriate position in the package of the light source apparatus 40, measures a temperature inside the package (room temperature) and outputs the measurement result to the control section 41.

The control section 41 receives the temperature measurement results from the thermistors 53 and 54, and controls the current value of the drive current of the Peltier element 56 according to the temperature measurement result. For example, the control section 41 performs control in such a way as to increase the current value of the drive current of the Peltier element 56 as the temperature in the vicinity of the R-LED 42 from the thermistor 53 increases, and decrease the current value of the drive current of the Peltier element 56 as the temperature decreases. For example, the control section 41 may also control the drive current of the Peltier element 56 using the temperature measurement results of the thermistor 54. For example, the control section 41 may control the drive current of the Peltier element 56 in such a way that the temperature in the vicinity of the R-LED 42 does not fall below the room temperature obtained from the thermistor 54.

Note that the light quantity of the R-LED 42 varies relatively largely depending on the temperature of the junction (semiconductor P-n junction) and the light quantity significantly decreases as the temperature increases. For this reason, to secure a sufficient light quantity as the red color, the R-LED 42 needs to be cooled to nearly a dew-point temperature. In this way, the R-LED 42 is more susceptible to temperatures than the LEDs 43 to 45 of the other colors and needs to be cooled sufficiently. For this reason, an example has been presented in the present embodiment where the Peltier element 56 is disposed only for the R-LED 42, but it is obvious that Peltier elements may be provided in all or some of the other LEDs 43 to 45. In this case, a drive current is caused to flow through each Peltier element in full synchronization with a drive pulse for driving each LED and the current value of the drive current to be supplied to each Peltier element is determined based on temperature measurement results and temperature in the package of the thermistor disposed in the vicinity of each LED, too.

Figure 2:
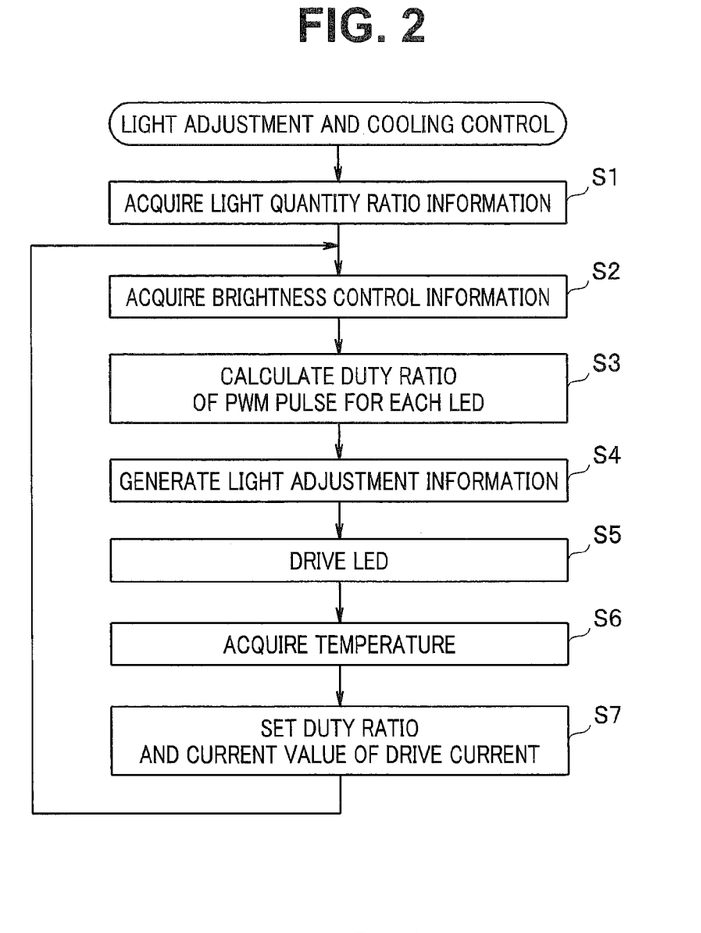
FIG. 2 is a flowchart for describing light adjustment and cooling control according to the embodiment.
Figure 3:
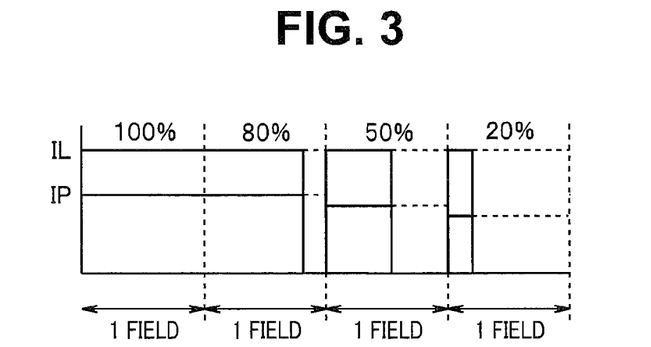
FIG. 3 is a diagram for describing a PWM pulse supplied to an R-LED 42 and a drive current supplied to a Peltier element 56.

Next, operation of the embodiment configured in this way will be described with reference to FIG. 2 and FIG. 3. FIG. 2 is a flowchart for describing light adjustment and cooling control according to the embodiment. FIG. 3 is a diagram illustrating a PWM pulse supplied to the R-LED 42 and a drive current supplied to the Peltier element 56.

When the power to the light source apparatus 40 is turned on, the control section 41 acquires information on a light quantity ratio from the memory section 51 (step S1). In step S2, the control section 41 acquires brightness control information from the video processor 20. The control section 41 accesses the memory section 51 based on the brightness control information, acquires a control value (duty ratio) for controlling the G-LED 43 which serves as a reference, and further calculates duty ratios of the other LEDs 42, 44 and 45 according to information on the light quantity ratios (step S4).

The control section 41 generates light adjustment information for specifying the duty ratio obtained for each LED 42 to 45 (step S4) and outputs the light adjustment information to the LED drive section 46 (step S5). The LED drive section 46 generates a PWM pulse with a duty ratio based on the light adjustment information and supplies the PWM pulse to each LED 42 to 45. Thereby, the LEDs 42 to 45 generate light with light quantities based on the light adjustment information. The emitted light beams of the LEDs 42 to 45 are synthesized by the dichroic filters 47 to 49 and the synthesized light is made incident on the light guide 15 as illuminating light via the lens 50. The illuminating light transmitted through the light guide 15 is radiated onto an object from the lens 14.

The image pickup device 13 receives reflected light from the object, photoelectrically converts the reflected light and obtains a picked-up image. The picked-up image is supplied to the video processor 20 via the signal line 16. The video processor 20 applies predetermined signal processing to the picked-up image to generate a video signal and supplies the video signal to the monitor 30 via the cable 21. In this way, an endoscope image is displayed on the display screen of the monitor 30.

The video processor 20 generates brightness control information through a comparison between brightness of the picked-up image and target brightness. For example, the video processor 20 generates brightness control information for each field and outputs the brightness control information to the control section 41 of the light source apparatus 40.

Thus, the control section 41 generates light adjustment information based on the brightness control information, for example, for each field and performs control so that the light quantity of the illuminating light from the synthesized light of emitted light beams from the LEDs 42 to 45 reaches the target brightness.

Furthermore, in step S6, the control section 41 acquires a temperature in the vicinity of the R-LED 42 and a temperature inside the package from the thermistors 53 and 54. The control section 41 generates a control signal for generating a drive current with the same duty ratio synchronized with the rise and fall of a PWM pulse supplied to the R-LED 42, which is a drive current with the current value corresponding to the temperature acquired in step S6, and outputs the control signal to the Peltier drive section 55 (step S7).

The Peltier drive section 55 generates a drive current of the Peltier element 56 under the control of a control signal from the control section 41. The drive current flows through the Peltier element 56 and the cooling surface of the Peltier element 56 is thereby cooled. For example, the control section 41 may acquire a temperature in the same cycle as the cycle of generation of brightness control information and generate a control signal as shown in the example of FIG. 2. In this case, the control section 41 generates a control signal for controlling the drive current based on the temperature acquired for each field and performs control so that the temperature in the vicinity of the R-LED 42 reaches the predetermined target temperature, for example.

Reference character IL in FIG. 3 denotes a PWM pulse to be supplied to the R-LED 42 and reference character IP denotes a drive current. As shown in FIG. 3, the drive current is synchronized with the PWM pulse and the drive current flows through the Peltier element 56 for the period during which the LED current flows through the R-LED 42, that is, the same period as the light emission period of the R-LED 42. Thus, when the R-LED 42 emits light and starts to generate heat, the R-LED 42 is cooled by the Peltier element 56. Furthermore, the current value of the drive current varies depending on the temperatures of the thermistors 53 and 54 and it is possible to keep the temperature in the vicinity of the R-LED 42 substantially constant.

In the example of FIG. 3, when the duty ratio of a PWM pulse to be supplied to the R-LED 42 decreases, the amount of light emission decreases and the temperature in the vicinity of the R-LED 42 decreases, the drive current also decreases and the cooling effect is reduced, with the result that the temperature in the vicinity of the R-LED 42 is kept substantially constant.

For example, when an observation scene using the endoscope 10 changes from a far point to a near point, the light quantity of the R-LED 42 drastically decreases under the brightness control by the control section 41 and the amount of heat generation also drastically decreases. In this case, a drive current of the Peltier element 56 is also generated in synchronization with the PWM pulse of the R-LED 42 and the current value of the drive current drastically decreases according to the measurement results of the thermistors 53 and 54, and therefore the cooling effect of the Peltier element 56 decreases, making it possible to prevent the temperature in the vicinity of the R-LED 42 from decreasing excessively. This can prevent condensation from occurring due to excessive cooling of the LED.

Conversely, when an observation scene using the endoscope 10 changes from a near point to a far point, the amount of heat generation also drastically increases as the light quantity of the LED increases. In this case, the current value of the drive current drastically increases according to the measurement results of the thermistors 53 and 54, and therefore the cooling effect of the Peltier element 56 drastically increases, making it possible to prevent the temperature in the vicinity of the R-LED 42 from increasing excessively.

Thus, the present embodiment causes a current to flow through the Peltier element to cool the corresponding LEDs at timing that matches the drive pulses of the LEDs and determines the current value of the drive current of each Peltier element based on a temperature in the vicinity of each LED and a temperature inside the package. In this way, cooling by the Peltier element is performed during a light emission period of the LED and the cooling effect of the Peltier element is controlled based on the temperature in the vicinity of each LED and the temperature inside the package, and it is thereby possible to control the cooling of each LED so as to reach an appropriate temperature. Thus, even when a light quantity variation and a temperature variation are relatively large, it is possible to perform cooling with excellent followability to the temperature variation.

However, in a high humidity environment, the dew-point temperature is relatively high and condensation is likely to occur. For example, when humidity is on the order of 85 RH %, the surface of the LED is likely to have a temperature equal to or lower than the dew-point temperature, subject to condensation. Condensation on the surface of the LED may cause a drop in the quantity of outgoing light or a failure. Therefore, a structure less susceptible to condensation is adopted as the structure of the LED light source.

First Example

Figure 4:
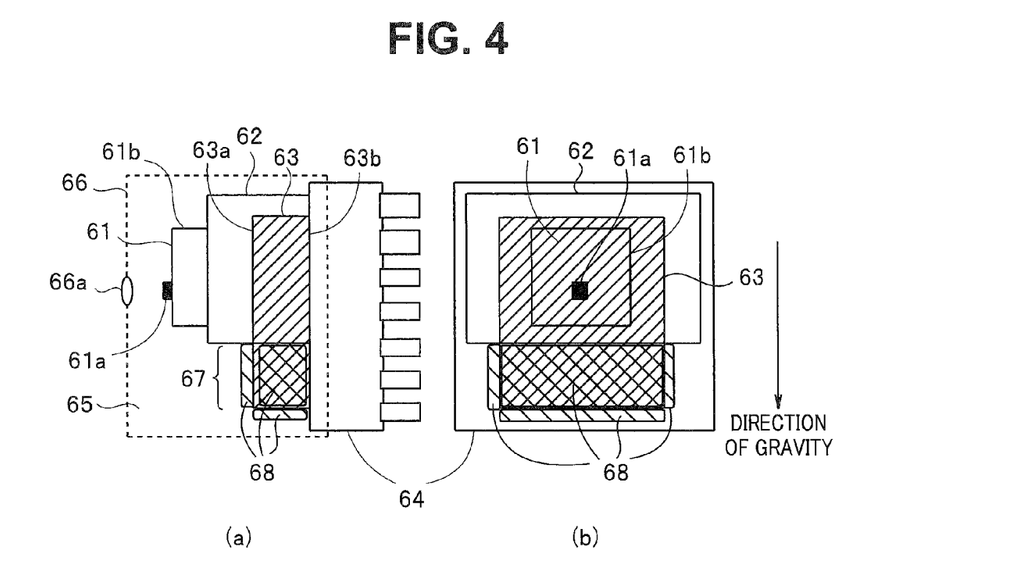
FIG. 4 is a diagram illustrating a structure of an LED light source less susceptible to condensation.

FIG. 4 illustrates a structure of an LED light source less susceptible to condensation, FIG. 4(a) showing a side view and FIG. 4(b) showing a plan view. The direction of gravity is indicated by an arrow in FIG. 4. An LED 61 includes a substrate 61b and a light emitting section 61a disposed on a front face of the substrate 61b. On a back side of the substrate 61b of the LED 61, a Peltier element 63 (shaded area) is disposed via a thermal diffusion plate 62. The Peltier element 63 is disposed on a heat sink 64 and a cooling surface (top surface and side face) 63a side is covered with the thermal diffusion plate 62. That is, the cooling surface 63a of the Peltier element 63 is in contact with the thermal diffusion plate 62 and a heat dissipation surface (bottom surface) 63b is in contact with the heat sink 64.

By causing a drive current to flow through the Peltier element 63, heat is transmitted from the cooling surface 63a of the Peltier element 63 to the heat dissipation surface 63b and the cooling surface 63a is cooled. The heat generated in the LED substrate 61b is transmitted to the cooling surface 63a of the cooled Peltier element 63 via the thermal diffusion plate 62 on the back side of the substrate 61b, the heat is further transmitted from the heat dissipation surface 63b of the Peltier element 63 to the heat sink 64 and dissipated. This can cause the temperature of the LED 61 to decrease.

The heat sink 64 is provided with a sealing member 66 that constitutes a sealing region 65 surrounding the Peltier element 63, the thermal diffusion plate 62 and the LED 61 disposed on the heat sink 64. A lens section 66a is formed at a position opposite to the light emitting section 61a of the LED 61 in the sealing member 66, which allows light from the light emitting section 61a to be radiated to the outside of the sealing region 65. Note that the sealing member 66 may be formed of a transparent member and the lens section 66a may be omitted.

In the example of FIG. 4, a lower part of the Peltier element 63 in the direction of gravity is not covered with the thermal diffusion plate 62 and part of the cooling surface 63a is exposed in the sealing region 65, constituting an atmosphere exposed surface 67.

In the LED light source configured in this way, the LED substrate 61b is cooled by causing a drive current to flow through the Peltier element 63. The Peltier element 63 is designed to cool the LED substrate 61b via the thermal diffusion plate 62 and the temperature of the LED substrate 61b is high relative to the cooling surface 63a of the Peltier element 63. Therefore, when the Peltier element 63 is driven, the temperature of the atmosphere exposed surface 67 which is part of the cooling surface 63a of the Peltier element 63 is lower than the temperature of the LED substrate 61b.

In the sealing region 65, condensation first occurs in a part where a surface temperature falls to or below the dew-point temperature, and water droplets caused by the condensation gather at the position where the condensation has occurred. In the example of FIG. 4, a temperature drop is largest on the cooling surface 63a inside the sealing region 65 when the Peltier element 63 is driven. Therefore, when condensation occurs, water droplets (shaded area and mesh pattern area) 68 due to condensation are first produced on the atmosphere exposed surface 67. When condensation occurs on the atmosphere exposed surface 67, much of the total water content in the sealing region 65 gathers in the vicinity of the atmosphere exposed surface 67, and therefore humidity in the sealing region 65 decreases. Thus, the dew-point temperature decreases inside the sealing region 65, whereas condensation is extremely unlikely to occur in areas other than the atmosphere exposed surface 67 and no condensation occurs in the LED 61 portion.

Furthermore, since the atmosphere exposed surface 67 is located on the lowest side in the sealing region 65 in the direction of gravity, the water droplets 68 gathering in this part are less likely to move to other parts. As a result, it is possible to reliably prevent water droplets due to condensation from adhering to the LED 61.

Note that a high thermal resistance member may be adopted as the thermal diffusion plate 62. In this case, the temperature difference between the cooling surface 63a and the LED substrate 61b becomes still greater. That is, the temperature of the atmosphere exposed surface 67 becomes still lower than the temperature of the LED 61. For this reason, condensation is more likely to occur in the vicinity of the atmosphere exposed surface 67 and it is possible to further prevent condensation from occurring in the LED 61.

Second Example

Figure 5:
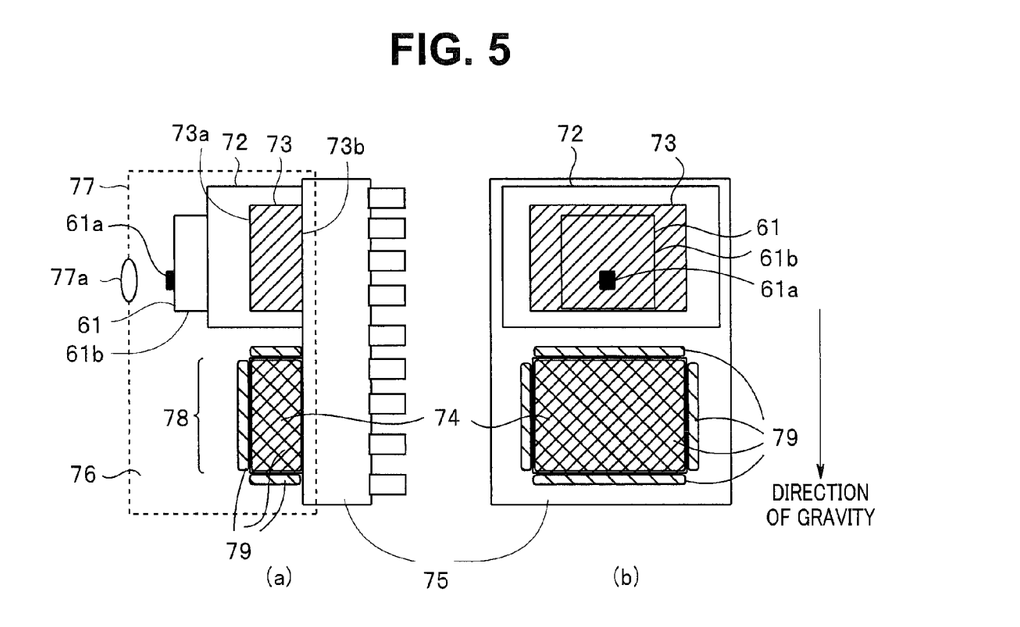
FIG. 5 is a diagram illustrating an example of another structure of the LED light source less susceptible to condensation.

FIG. 5 shows an example of another structure of the LED light source less susceptible to condensation, FIG. 5(a) showing a side view and FIG. 5(b) showing a plan view. The direction of gravity is indicated by an arrow in FIG. 5, too. The LED 61 includes the substrate 61b and the light emitting section 61a disposed on the front face of the substrate 61b. A Peltier element 73 (shaded area) is disposed on the back side of the substrate 61b of the LED 61 via a thermal diffusion plate 72. The Peltier element 73 is disposed on a heat sink 75 and a cooling surface (top surface and side face) 73a side is covered with the thermal diffusion plate 72. That is, the cooling surface 73a of the Peltier element 73 is in contact with the thermal diffusion plate 72 and a heat dissipation surface (bottom surface) 73b is in contact with the heat sink 75.

By causing a drive current to flow through the Peltier element 73, heat is transmitted from the cooling surface 73a of the Peltier element 73 to the heat dissipation surface 73b and the cooling surface 73a is cooled. The heat generated in the LED substrate 61b is transmitted to the cooling surface 73a of the cooled Peltier element 73 via the thermal diffusion plate 72 on the back side of the substrate 61b, and further transmitted from the heat dissipation surface 73b of the Peltier element 73 to the heat sink 75 and dissipated. This can cause the temperature of the LED 61 to decrease.

A sealing member 77 is provided on the heat sink 75, which constitutes a sealing region 76 surrounding the Peltier element 73, the thermal diffusion plate 72 and the LED 61 which are provided on the heat sink 75. A lens section 77a is formed at a position opposite to the light emitting section 61a of the LED 61 in the sealing member 77, which allows light from the light emitting section 61a to be radiated to the outside of the sealing region 76. Note that the sealing member 77 may be formed of a transparent member and the lens section 77a may be omitted.

In the example of FIG. 5, the cooling surface (top surface and side face) is exposed inside the sealing region 76 and a Peltier element 74 that constitutes an atmosphere exposed surface 78 is disposed in a lower partial region in the direction of gravity inside the sealing region 76. The heat dissipation surface (bottom surface) of the Peltier element 74 is in contact with the heat sink 75.

In the LED light source configured in this way, the LED substrate 61b is cooled by causing a drive current to flow through the Peltier element 73. Furthermore, by causing a drive current to flow through the Peltier element 74, the cooling surface of the Peltier element 74 is cooled. The Peltier element 73 is intended to cool the LED substrate 61b via the thermal diffusion plate 72 and the temperature of the LED substrate 61b is high relative to the cooling surface 73a of the Peltier element 73. Therefore, when the cooling effect of the Peltier element 74 is equal to or greater than the cooling effect of the Peltier element 73, the temperature of the atmosphere exposed surface 78 which is the cooling surface of the Peltier element 74 is lower than the temperature of the LED substrate 61b when the Peltier elements 73 and 74 are being driven.

In the sealing region 76, condensation first occurs in a part where a surface temperature falls to or below the dew-point temperature, and water droplets caused by the condensation gather at the position where the condensation has occurred. Therefore, in the example of FIG. 5, when condensation occurs, water droplets (shaded area and mesh pattern area) 79 caused by the condensation are first produced in the atmosphere exposed surface 78. When condensation occurs on the atmosphere exposed surface 78, much of the total water content in the sealing region 76 gathers in the vicinity of the atmosphere exposed surface 78, and therefore humidity in the sealing region 76 decreases. Thus, in the sealing region 76, condensation is extremely unlikely to occur in portions other than the atmosphere exposed surface 78 and no condensation occurs in the LED 61 portion.

Furthermore, since the atmosphere exposed surface 78 is located on the lowest side in the sealing region 76 in the direction of gravity, the water droplets 79 gathering in this part are less likely to move to other parts. As a result, it is possible to reliably prevent water droplets due to condensation from adhering to the LED 61.

Third Example

Figure 6:
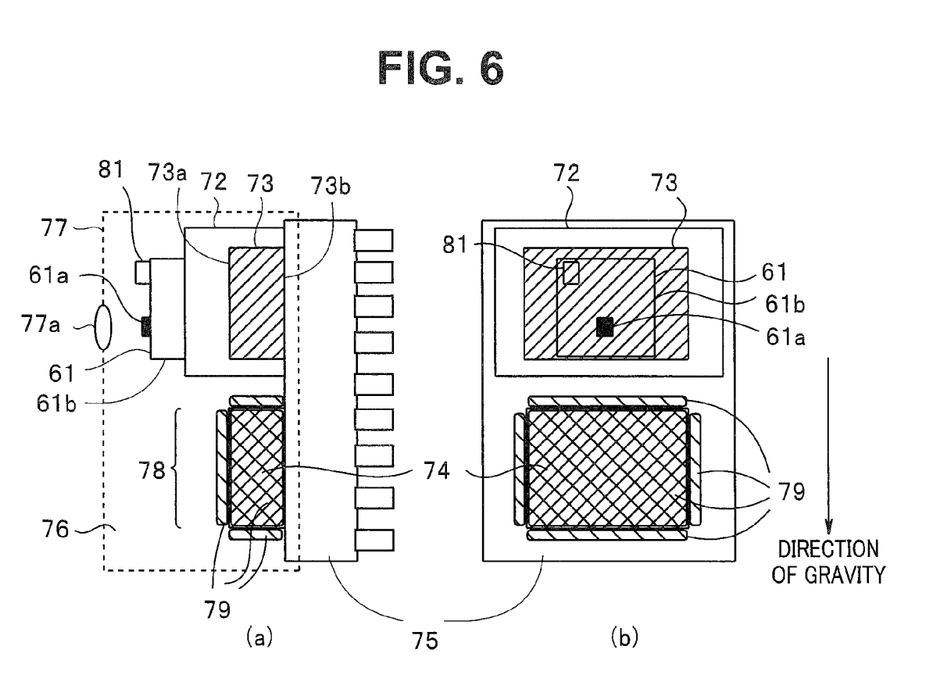
FIG. 6 is a diagram illustrating an example of a further structure of the LED light source less susceptible to condensation.

FIG. 6 illustrates an example of another structure of the LED light source less susceptible to condensation, FIG. 6(*a*) showing a side view and FIG. 6(*b*) showing a plan view. The direction of gravity is indicated by an arrow in FIG. 6, too. The third example is only different from the second example in FIG. 5 in that a temperature and humidity sensor 81 is provided. The temperature and humidity sensor 81 is designed to be able to measure temperature and humidity in the vicinity of the LED 61. The measurement results of the temperature and humidity sensor 81 are supplied to a control section, which is not shown, that controls driving of the Peltier elements 73 and 74. This control section drives only the Peltier element 73 in an initial state.

The control section obtains a dew-point temperature from the temperature and humidity of the measurement results and determines whether or not the temperature in the vicinity of the LED 61 is about to reach the dew-point temperature or below. The control section is designed to drive the Peltier element 74 only when the temperature in the vicinity of the LED 61 is about to reach the dew-point temperature or below. Thus, the portion of the atmosphere exposed surface 78 of the Peltier element 74 falls to or below the dew-point temperature first and condensation occurs on the atmosphere exposed surface 78. This can prevent condensation from occurring in the LED 61.

The present invention is not limited to the above-described embodiment as it is, but can be implemented by modifying the components without departing from the spirit and scope of the present invention in an implementation phase. Furthermore, various inventions can be formed by appropriately combining the plurality of components disclosed in each of the above-described embodiments. For example, several components of all the components shown in the embodiment may be deleted. Moreover, components among different embodiments may be combined as appropriate.

[Notes]

1.
A light source apparatus comprising:
a semiconductor light-emitting device;
a cooling device that comprises a temperature-controlled cooling surface and cools the semiconductor light-emitting device;
a thermal diffusion member that is provided so as to cover the cooling surface other than a lower side portion of the cooling device in a direction of gravity, interposed between the semiconductor light-emitting device and the cooling device and transmits heat generated in the semiconductor light-emitting device to the cooling surface; and
a sealing member that houses the semiconductor light-emitting device, the cooling device and the thermal diffusion member in an airtight space.

2.
A light source apparatus comprising:
a semiconductor light-emitting device;
a first cooling device that comprises a first temperature-controlled cooling surface and cools the semiconductor light-emitting device;
a thermal diffusion member that is provided so as to cover the first cooling surface, interposed between the semiconductor light-emitting device and the first cooling device and transmits heat generated in the semiconductor light-emitting device to the first cooling surface;
a sealing member that houses the semiconductor light-emitting device, the first cooling device and the thermal diffusion member in an airtight space; and
a second cooling device that comprises a second temperature-controlled cooling surface, is disposed on a lower side of the semiconductor light-emitting device in a direction of gravity in the airtight space and cools the airtight space through the second cooling surface.

What is claimed is:
1. A light source apparatus comprising:
a semiconductor light-emitting device;
a cooling device configured to be able to cool the semiconductor light-emitting device;
a semiconductor light-emitting device drive section that supplies, to the semiconductor light-emitting device, a semiconductor light-emitting device drive signal for causing the semiconductor light-emitting device to emit light;
a cooling device drive section that supplies, to the cooling device, a cooling device drive signal for causing the cooling device to cool the semiconductor light-emitting device;
a semiconductor light-emitting device drive control section that sets a duty ratio of the semiconductor light-emitting device drive signal and controls an amount of light emission of the semiconductor light-emitting device;
a temperature sensor that measures a temperature of the semiconductor light-emitting device; and
a cooling device drive control section that controls the cooling device drive section so as to generate the cooling device drive signal having a same duty ratio as the duty ratio of the semiconductor light-emitting device drive signal set by the semiconductor light-emitting device drive control section and having timing synchronized with the semiconductor light-emitting device drive signal and controls the cooling device drive section so as to adjust a signal level of the cooling device drive signal based on a measurement result of the temperature sensor.

2. The light source apparatus according to claim 1, wherein the cooling device drive control section adjusts a signal level of the cooling device drive signal so that the measurement result of the temperature sensor falls within a predetermined temperature range.

3. The light source apparatus according to claim 1, further comprising a room temperature sensor that measures a room temperature,
wherein the cooling device drive control section adjusts a signal level of the cooling device drive signal based on measurement results of the temperature sensor and the room temperature sensor.

4. The light source apparatus according to claim 3, wherein the cooling device drive control section adjusts the signal level of the cooling device drive signal so that the measurement result of the temperature sensor becomes higher than the measurement result of the room temperature sensor.

5. An endoscope apparatus comprising:
an endoscope;
a semiconductor light-emitting device that generates illuminating light to be supplied to the endoscope;
a cooling device configured to be able to cool the semiconductor light-emitting device;

a semiconductor light-emitting device drive section that supplies, to the semiconductor light-emitting device, a semiconductor light-emitting device drive signal for causing the semiconductor light-emitting device to emit light;

a cooling device drive section that supplies, to the cooling device, a cooling device drive signal for causing the cooling device to cool the semiconductor light-emitting device;

a semiconductor light-emitting device drive control section that sets a duty ratio of the semiconductor light-emitting device drive signal and controls an amount of light emission of the semiconductor light-emitting device;

a temperature sensor that measures a temperature of the semiconductor light-emitting device; and a cooling device drive control section that controls the cooling device drive section so as to generate the cooling device drive signal having a same duty ratio as the duty ratio of the semiconductor light-emitting device drive signal set by the semiconductor light-emitting device drive control section and having timing synchronized with the semiconductor light-emitting device drive signal and controls the cooling device drive section so as to adjust a signal level of the cooling device drive signal based on a measurement result of the temperature sensor.

6. The endoscope apparatus according to claim 5, further comprising a video processor that applies predetermined signal processing to an image pickup output from the endoscope to generate a video signal, controls the semiconductor light-emitting device drive control section so that brightness of an image based on the video signal becomes target brightness and causes the amount of light emission of the semiconductor light-emitting device to vary.

* * * * *